United States Patent [19]
Wierzbicki et al.

[11] Patent Number: 5,849,745
[45] Date of Patent: Dec. 15, 1998

[54] N-BENZYLPIPERAZINE COMPOUNDS

[75] Inventors: Michel Wierzbicki, L'Etang la Ville; Marie-Françoise Boussard, Mareil Sur Mauldre; Serge Labidalle, Pinsaguel; Daniel Guyot, Montjoire; Yves Rolland, Vanves; Jean-Paul Tillement, Bois le Roi, all of France; Bernard Testa, Lausanne, Switzerland; Aimé Crevat, Marseilles, France

[73] Assignee: ADIR et Compagnie, Courbevoie, France

[21] Appl. No.: 990,611

[22] Filed: Dec. 15, 1997

[30] Foreign Application Priority Data

Dec. 16, 1996 [FR] France .................. 96 15415

[51] Int. Cl.$^6$ .................. A61K 31/495; C07D 295/116; C07D 401/12; C07D 405/12
[52] U.S. Cl. .................. 514/252; 514/255; 544/365; 544/372; 544/376; 544/394; 544/399; 544/374
[58] Field of Search .................. 544/365, 372, 544/374, 376, 394, 399; 514/252, 255

[56] References Cited

U.S. PATENT DOCUMENTS

| | | | |
|---|---|---|---|
| 2,927,924 | 3/1960 | Mills | 544/394 |
| 3,262,852 | 7/1966 | Servier | 544/394 |
| 5,283,246 | 2/1994 | Regnier et al. | 514/255 |
| 5,492,913 | 2/1996 | Wierzbicki et al. | 514/255 |

*Primary Examiner*—Emily Bernhardt
*Attorney, Agent, or Firm*—The Firm of Gordon W. Hueschen

[57] ABSTRACT

A compound of formula (I):

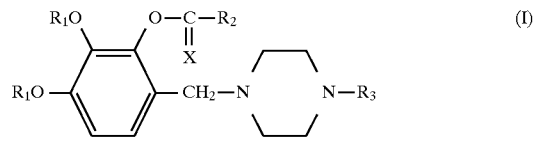

In which:
- $R_1$ represents linear or branched ($C_1$–$C_6$) alkyl,
- X represents oxygen or sulfur,
- $R_2$ represents optionally substituted alkyl, alkoxy, optionally substituted phenyl, optionally substituted cycloalkyl, 4-(2,3-dithiacyclopent-1-yl)butyl, pyridyl or optionally substituted amino or any one of the groups as defined in the description,
- $R_3$ represents hydrogen or cycloalkyl, formyl, optionally substituted phenyl, pyridyl or optionally substituted alkyl, the isomers thereof, the addition salts thereof with a pharmaceutically acceptable acid or base, and medicinal compounds containing them are useful for the treatment of chronic or cellular ischemia.

10 Claims, No Drawings

N-BENZYLPIPERAZINE COMPOUNDS

FIELD OF THE INVENTION

The present invention relates to new N-benzylpiperazine compounds.

PRIOR ART DESCRIPTION

The prior art is illustrated in particular by:

French patents 1,302,958 and 805M, which relate respectively to the preparation of N-(trialkoxybenzyl) piperazines and to the use, as medicament with a vasodilatory action, of (2,3,4-trimethoxybenzyl) piperazine, the articles by Hiroshi Ohtaka et al., Chem. Pharm. Bull., 35, 2774–3275 (1987) and Chem. Pharm. Bull., 37, 11, 2124–3122 (1989) which mention trimetazidine derivatives having a vasodilatory activity and the synthesis of 1-[bis(4-fluorophenyl)methyl]-4-(2-hydroxy-3,4-dimethoxy benzyl)piperazine, the article by Tsuneo Kawashima et al., J. Pharmacobio-Dyn, 14, 449–459 (1991) relating to the isolation and the identification of novel metabolites of KB-2796, including, inter alia, 1-[bis(4-fluorophenyl)methyl]-4-(2-hydroxy-3,4-dimethoxybenzyl)piperazine, European patent EP 533,579, which describes N-benzylpiperazine derivatives having an antihypoxic and antiischemic activity, finally, European patent EP 617,027, which describes N-benzylpiperazine derivatives useful in the treatment of neuronal diseases due to dysfunctioning of the oxidative metabolism.

BACKGROUND OF THE INVENTION

Besides the fact that they are novel, the derivatives of the present invention have a pharmacological activity and therapeutic properties that are particularly advantageous.

They allow, inter alia, the protection of mitochondria subjected to hypoxic stress, the restoration of ATP synthesis by oxygen-starved organs and the protection of an isolated heart placed under ischemic conditions. Lastly, they are capable of crossing the blood/brain barrier. These properties thus make them useful for the treatment of chronic cellular ischemia, acute cerebral, cardiac or peripheral ischemic accidents, for the treatment of chronic neurodegenerative diseases (such as Alzheimer's disease or Parkinson's disease) and for improving the storage of organs intended for transplants and the survival of grafts during reinfusion stress.

DETAILED DESCRIPTION OF THE INVENTION

More specifically, the present invention relates to the compounds of formula (I):

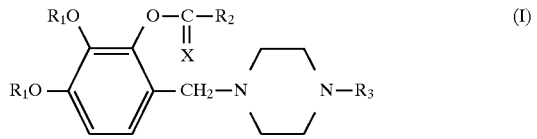

in which:

$R_1$ represents a linear or branched ($C_1$–$C_6$)alkyl group,

X represents an oxygen or sulfur atom, $R_2$ represents a linear or branched ($C_1$–$C_8$)alkyl group (optionally substituted with a linear or branched carboxyl or ($C_1$–$C_6$)alkoxycarbonyl group), a linear or branched ($C_1$–$C_6$)alkoxy group, a phenyl group (optionally substituted with one or more halogen atoms or linear or branched ($C_1$–$C_6$)alkyl groups, linear or branched ($C_1$–$C_6$)alkoxy groups, hydroxyl or trihalomethyl groups), a ($C_3$–$C_7$)cycloalkyl group (optionally substituted with one or more phenyl groups which are themselves optionally substituted with one or more halogen atoms or linear or branched ($C_1$–$C_6$)alkyl groups, linear or branched ($C_1$–$C_6$)alkoxy groups, hydroxyl or trihalomethyl groups), a 4-(2,3-dithiacyclopent-1-yl) butyl group, a pyridyl group, an amino group (optionally substituted with one or two linear or branched ($C_1$–$C_6$)alkyl groups), or any one of the following groups:

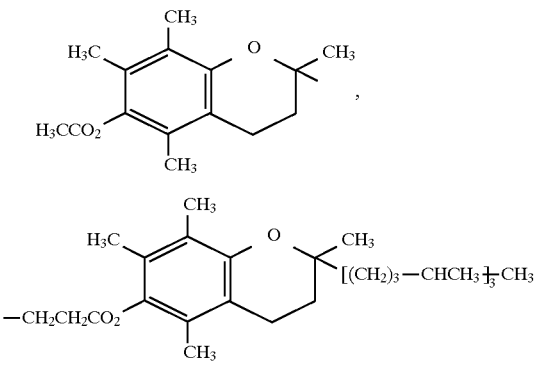

$R_3$ represents a hydrogen atom, a ($C_3$–$C_7$)cycloalkyl group, a formyl group, a phenyl group (optionally substituted with one or more halogen atoms or linear or branched ($C_1$–$C_6$)alkyl groups, linear or branched ($C_1$–$C_6$)alkoxy groups, hydroxyl or trihalomethyl groups), a pyridyl group, or a linear or branched ($C_1$–$C_{20}$)alkyl group optionally substituted with one or more, identical or different, halogen atoms or groups below:

phenyl optionally substituted with one or more halogen atoms or linear or branched ($C_1$–$C_6$)alkyl groups, linear or branched ($C_1$–$C_6$)alkoxy groups, hydroxyl or trihalomethyl groups, ($C_3$–$C_7$)cycloalkyl optionally substituted with one or more phenyl groups which are themselves optionally substituted with one or more halogen atoms or linear or branched ($C_1$–$C_6$)alkyl groups, linear or branched ($C_1$–$C_6$)alkoxy groups, hydroxyl or trihalomethyl groups, linear or branched ($C_1$–$C_6$)alkoxy, hydroxyl or pyrrolidinyl, the isomers thereof and the addition salts thereof with a pharmaceutically acceptable acid or base.

Among the pharmaceutically acceptable acids, mention may be made, in a nonlimiting manner, of hydrochloric acid, hydrobromic acid, sulfuric acid, phosphonic acid, acetic acid, trifluoroacetic acid, lactic acid, pyruvic acid, malonic acid, succinic acid, glutaric acid, fumaric acid, tartaric acid, maleic acid, citric acid, ascorbic acid, oxalic acid, methanesulfonic acid, camphoric acid, etc.

Among the pharmaceutically acceptable bases, mention may be made, in a nonlimiting manner, of sodium hydroxide, potassium hydroxide, triethylamine, tert-butylamine, etc.

The invention also covers the process for the preparation of the compounds of formula (I), wherein the starting material used is a compound of formula (II):

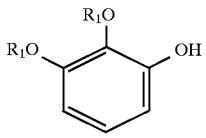

in which $R_1$ has the same meaning as in formula (I), which compound is reacted with a substituted piperazine of formula (III):

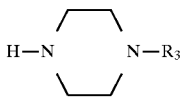

in which $R_3$ has the same meaning as in formula (I), in the presence of formaldehyde, in order to give the compound of formula (IV);

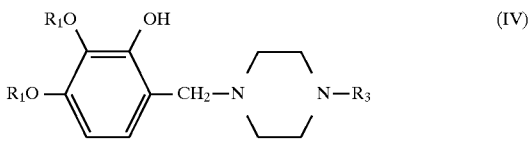

in which $R_1$ and $R_3$ have the same meaning as in formula (I), which compound is then reacted with a carboxylic acid of formula $R_2CO_2H$ (in which $R_2$ has the same meaning as in formula (I), an alkyl chloroformate, an acid chloride of formula $R_2COCl$ (in which $R_2$ has the same meaning as above), an acid anhydride or a chlorocarbamate, in order to give the compound of formula (I/a), which is a specific case of the compounds of formula (I):

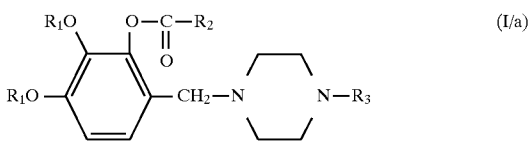

in which $R_1$, $R_2$ and $R_3$ have the same meaning as above, which compound of formula (I/a) is optionally subjected to the action of Lawesson's reagent, in order to give the corresponding thioester of formula (I/b), which is a specific case of the compounds of formula (I):

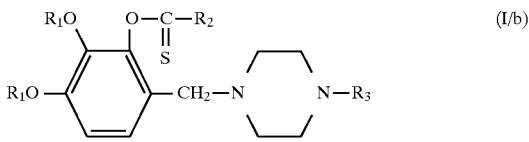

in which $R_1$, $R_2$ and $R_3$ have the same meaning as in formula (I), which compounds of formula (I/a) or (I/b)
are purified, where appropriate, according to a standard purification technique, whose isomers are optionally separated, and which are converted, if so desired, into the addition salt with a pharmaceutically acceptable acid or base.

The compounds of the invention in which $R_3$ represents a hydrogen atom are more particularly obtained from the compound of formula (I/a) in which $R_3$ represents a benzyl group, which is subjected to catalytic hydrogenation in dimethylformamide.

The preferred compounds of the invention are the compounds of formula (I) in which $R_1$ represents a methyl group and X represents an oxygen atom.

Among the preferred compounds of the invention for which $R_1$ represents a methyl group and X represents an oxygen atom, the preferred substituent $R_2$ is the optionally substituted $(C_3-C_7)$cycloalkyl group and more particularly the phenylcyclopropyl group. The preferred substituent $R_3$ is the optionally substituted alkyl group and more particularly the ethyl or benzyl group.

A subject of the present invention is also the pharmaceutical compositions containing, as active principle, at least one compound of formula (I), alone or in combination with one or more inert, nontoxic excipients or vehicles.

Among the pharmaceutical compositions according to the invention, mention may be made more particularly of those which are suitable for oral, parenteral and nasal administration, simple or sugar-coated tablets, sublingual tablets, gelatin capsules, lozenges, suppositories, creams, ointments, dermal gels, etc.

The working dosage varies depending on the patient's age and weight, the nature and severity of the complaint and the route of administration. This may be the oral, nasal, rectal or parenteral route. In general, the unit dosage ranges between 0.1 and 500 mg for a treatment of 1 to 3 doses per 24 hours.

The examples which follow illustrate the invention but do not limit it in any way.

The starting materials used are known products or products which are prepared according to known procedures.

The structures of the compounds described in the examples were determined according to the usual spectrophotometric techniques (infrared, NMR, mass spectrometry, etc.).

EXAMPLE

N-(3,4-Dimethoxy-2-E-phenylcyclopropylcarbonyloxy)benzyl-N'-ethylpiperazine dihydrochloride Stage A: N-(3,4-Dimethoxy-2-hydroxy)benzyl-N'-ethylpiperazine 56 mmol of N-ethylpiperazine in 100 ml of ethanol and 56 mmol of 2,3-dimethoxyphenol in 100 ml of ethanol are added simultaneously into a reactor while stirring vigorously at room temperature. 45 ml of aqueous 38% W/V formaldehyde solution is added dropwise to this solution. The reaction medium is stirred for 24 hours at room temperature and is then evaporated to dryness under partial vacuum.

The residue obtained is chromatographed on silica gel with a dichloromethane/methanol eluent mixture (97/3) and gives the expected product.

Stage B: N-(3,4-Dimethoxy-2-E-phenylcyclopropylcarbonyloxy)benzyl-N'-ethylpiperazine dihydrochloride To a solution of 40 mmol of 2-E-phenylcyclopropylcarboxylic acid in a mixture of dichloromethane and dimethylformamide (90/10) maintained at 0° C. under an inert atmosphere is added dropwise, with stirring, a solution of 120 mmol of oxalyl chloride in 20 ml of dichloromethane. The reaction medium is maintained at 0° C. for one hour and then at 25° C. for 12 hours. The excess oxalyl chloride and the solvent are evaporated off under partial vacuum and the residue obtained is taken up in 20 ml of dichloromethane.

The solution thus obtained is added dropwise to a solution of 40 mmol of the compound obtained in the above stage in 150 ml of anhydrous pyridine. The reaction medium is stirred at 25° C. for 24 hours and is then evaporated to dryness under partial vacuum.

The residue obtained is chromatographed on silica gel with a dichloromethane/methanol eluent mixture (95/5) and gives the expected product in the form of the base. This compound is dissolved in the minimum amount of anhydrous ether and is then added to twice the stoichiometric amount of HCl dissolved in anhydrous ether. An abundant precipitate forms immediately. It is collected by filtration and recrystallized from an ethanol/ether mixture. The dihydrochloride precipitate is filtered off and recrystallized from an ethanol/ether mixture.

| Elemental microanalysis: | | | |
|---|---|---|---|
| | C % | H % | N % |
| calculated | 60.36 | 6.89 | 5.63 |
| found | 60.30 | 6.89 | 5.65 |
| Melting point: 222° C. | | | |

EXAMPLE 2

N-(3,4-Dimethoxy-2-E-phenylcyclopropylcarbonyloxy)benzyl-N'-benzylpiperazine dihydrochloride The expected product is obtained according to the process described in Example 1, replacing the N-ethylpiperazine in Stage A by N-benzylpiperazine.

| Elemental microanalysis: | | | |
|---|---|---|---|
| | C % | H % | N % |
| calculated | 62.39 | 6.63 | 4.85 |
| found | 62.23 | 6.34 | 4.97 |
| Melting point: 216° C. | | | |

EXAMPLE 3

N-(2-Benzoyloxy-3,4-dimethoxy)benzyl-N'-benzylpiperazine dihydrochloride

The expected product is obtained according to the process described in Example 1, replacing the N-ethylpiperazine in Stage A by N-benzylpiperazine and the 2-E-phenylcyclopropylcarboxylic acid in Stage B by benzoic acid.

| Elemental microanalysis: | | | |
|---|---|---|---|
| | C % | H % | N % |
| calculated | 62.43 | 6.21 | 5.39 |
| found | 62.85 | 6.18 | 5.39 |
| Melting point: 210° C. | | | |

The following examples were prepared according to the process described in Example 1, using the corresponding starting materials.

EXAMPLE 4

N-(2-Benzoyloxy-3,4-dimethoxy)benzyl-N'-ethylpiperazine dihydrochloride

| Elemental microanalysis: | | | |
|---|---|---|---|
| | C % | H % | N % |
| calculated | 57.77 | 6.61 | 6.12 |
| found | 57.97 | 6.80 | 6.42 |
| Melting point: 205° C. (dec.) | | | |

EXAMPLE 5

N-(2-Acetoxy-3,4-dimethoxy)benzyl-N'-ethylpiperazine dihydrochloride

| Elemental microanalysis: | | | |
|---|---|---|---|
| | C % | H % | N % |
| calculated | 51.65 | 7.14 | 7.09 |
| found | 51.55 | 6.95 | 7.32 |
| Melting point: 230° C. (dec.) | | | |

EXAMPLE 6

N-(2-Acetoxy-3,4-dimethoxy)benzyl-N'-benzylpiperazine dihydrochloride

| Elemental microanalysis: | | | |
|---|---|---|---|
| | C % | H % | N % |
| calculated | 57.77 | 6.61 | 6.12 |
| found | 58.05 | 6.57 | 6.10 |
| Melting point: 220° C. (dec.) | | | |

EXAMPLE 7

N-(2-tert-Butylcarbonyloxy-3,4-dimethoxy)benzyl-N'-ethylpiperazine dihydrochloride

EXAMPLE 8

N-(2-tert-Butylcarbonyloxy-3,4-dimethoxy)benzyl-N'-benzylpiperazine dihydrochloride

EXAMPLE 9

N-(3,4-Dimethoxy-2-octanoyloxy)benzyl-N'-ethylpiperazine dihydrochloride

EXAMPLE 10

N-(3,4-Dimethoxy-2-octanoyloxy)benzyl-N'-benzylpiperazine dihydrochloride

EXAMPLE 11

N-(3,4-Dimethoxy-2-nicotinoyloxy)benzyl-N'-ethylpiperazine trihydrochloride

| Elemental microanalysis: | | | |
|---|---|---|---|
| | C % | H % | N % |
| calculated | 50.97 | 6.11 | 8.49 |
| found | 50.44 | 6.24 | 8.26 |
| Melting point: 180° C. | | | |

EXAMPLE 12

N-(3,4-Dimethoxy-2-nicotinoyloxy)benzyl-N'-benzylpiperazine trihydrochloride

| Elemental microanalysis: | | | |
|---|---|---|---|
| | C % | H % | N % |
| calculated | 56.07 | 5.79 | 7.55 |
| found | 56.19 | 5.53 | 7.56 |
| Melting point: 213° C. | | | |

EXAMPLE 13

N-[2-(6'-Acetoxy-2',5',7',8'-tetramethylchroman-2-ylcarbonyloxy)-3,4-dimethoxy]benzyl-N'-ethylpiperazine dihydrochloride

| Elemental microanalysis: | | | |
|---|---|---|---|
| | C % | H % | N % |
| calculated | 59.33 | 7.07 | 4.46 |
| found | 58.97 | 7.10 | 4.18 |
| Melting point: 215° C. | | | |

EXAMPLE 14

N-[2-(6'-Acetoxy-2',5',7',8'-tetramethylchroman-2-ylcarbonyloxy)-3, 4-dimethoxy]benzyl-N'-benzylpiperazine dihydrochloride

| Elemental microanalysis: | | | |
|---|---|---|---|
| | C % | H % | N % |
| calculated | 62.70 | 6.72 | 4.06 |
| found | 62.58 | 6.97 | 4.27 |
| Melting point: 227° C. | | | |

EXAMPLE 15

N-{2-[5-(2,3-dithiacyclopent-1-yl)Propanoyloxy-3,4-dinethoxy}benzyl-N'-ethylpiperazine dihydrochloride

| Elemental microanalysis: | | | |
|---|---|---|---|
| | C % | H % | N % |
| calculated | 51.01 | 7.07 | 5.17 |
| found | 50.67 | 6.71 | 4.78 |
| Melting point: 204° C. | | | |

EXAMPLE 16

N-{2-[5-(2,3-dihiacyclopent-1-yl)Propanoyloxy-3,4-dinethoxy}benzyl-N'-benzylpiperazine dihydrochloride

| Elemental microanalysis: | | | |
|---|---|---|---|
| | C % | H % | N % |
| calculated | 55.71 | 6.68 | 4.64 |
| found | 55.92 | 6.52 | 4.81 |
| Melting point: 220° C. (dec.) | | | |

EXAMPLE 17

N-(3,4-Dimethoxy-2-E-(R,R)-phenylcyclopropylcarbonyloxy)benzyl-N'-ethylpiperazine dihydrochloride

| Elemental microanalysis: | | | |
|---|---|---|---|
| | C % | H % | N % |
| calculated | 60.36 | 6.89 | 5.63 |
| found | 60.30 | 6.89 | 5.65 |
| Melting point: 200° C. | | | |

EXAMPLE 18

N-(3,4-Dimethoxy-2-E-(R,R)-phenylcyclopropylcarbonyloxy)benzyl-N'-benzyl-piperazine dihydrochloride Elemental microanalysis:

|  | C % | H % | N % |
|---|---|---|---|
| calculated | 64.40 | 6.49 | 5.01 |
| found | 64.35 | 6.76 | 4.82 |

Melting point: 206° C.

EXAMPLE 19

N-(3,4-Dimethoxy-2-E-(S,S)-phenylcyclopropylcarbonyloxy)benzyl-N'-ethylpiperazine dihydrochloride Elemental microanalysis:

|  | C % | H % | N % |
|---|---|---|---|
| calculated | 60.36 | 6.89 | 5.63 |
| found | 60.30 | 6.89 | 5.65 |

Melting point: 210° C.

EXAMPLE 20

N-(3,4-Dimethoxy-2-E-(S,S)-phenylcyclopropylcarbonyloxy)benzyl-N'-benzylpiperazine dihydrochloride Elemental microanalysis:

|  | C % | H % | N % |
|---|---|---|---|
| calculated | 64.40 | 6.49 | 5.01 |
| found | 64.25 | 6.32 | 5.23 |

Melting point: 205° C.

EXAMPLE 21

N-[3,4-Dimethoxy-2-(3-carboxypropionyloxy)]benzyl-N'-ethylpiperazine dihydrochloride

EXAMPLE 22

N-[3,4-Dimethoxy-2-(3-carboxypropionyloxy)]benzyl-N'-benzylpiperazine dihydrochloride

EXAMPLE 23

N-[3,4-Dimethoxy-2-(7-methoxycarbonylheptanoyloxy)]benzyl-N'-ethylpiperazine dihydrochloride

EXAMPLE 24

N-[3,4-Dimethoxy-2-(7-methoxycarbonylheptanoyloxy)]benzyl-N'-benzylpiperazine dihydrochloride

EXAMPLE 25

N-[3,4-Dimethoxy-2-(3-tocopheroylpropionyloxy)]benzyl-N'-ethylpiperazine dihydrochloride Tocopheroyl represents the group:

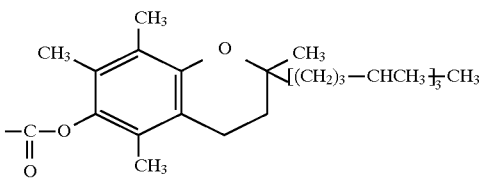

Elemental microanalysis:

|  | C % | H % | N % |
|---|---|---|---|
| calculated | 66.57 | 9.08 | 3.23 |
| found | 66.42 | 9.35 | 3.50 |

Melting point: 190° C.

EXAMPLE 26

N-[3,4-Dimethoxy-2-(3-tocopheroylpropionyloxy)]benzyl-N'-benzylpiperazine dihydrochloride Elemental microanalysis:

|  | C % | H % | N % |
|---|---|---|---|
| calculated | 68.59 | 8.69 | 3.02 |
| found | 68.32 | 8.92 | 3.24 |

Melting point: 206° C.

EXAMPLE 27

N-(2-Ethoxycarbonyloxy-3,4-dimethoxy)benzyl-N'-benzylpiperazine dihydrochloride To a solution of 10 mmol of N-benzyl-N'-(3,4-dimethoxy-2-hydroxy)benzyl-piperazine in 100 ml of anhydrous dichloromethane are added dropwise 11 mmol of a solution of ethyl chloroformate in 10 ml of dichloromethane. After stirring at room temperature for 24 h, the formation of a precipitate is observed. After neutralizing with aqueous sodium carbonate solution, the reaction medium is extracted with dichloromethane and the organic phase is concentrated to dryness under partial vacuum, and the residue is chromatographed on a column of silica (eluent: 95/5 dichloromethane/methanol). The fractions retained are combined and then concentrated under partial vacuum.

10 mmol of the compound thus obtained dissolved in the minimum amount of anhydrous ether are added to twice the stoichiometric amount of HCl dissolved in anhydrous ether. An abundant precipitate forms immediately, and is filtered off and recrystallized from an ethanol/ether mixture to give the expected product.

| Elemental microanalysis: | | | |
|---|---|---|---|
| | C % | H % | N % |
| calculated | 56.68 | 6.62 | 5.75 |
| found | 56.42 | 6.85 | 5.42 |
| Melting point: 223° C. | | | |

EXAMPLE 28

N-(2-Ethoxycarbonyloxy-3,4-dimethoxy)benzyl-N'-ethylpiperazine dihydrochloride

The expected product is obtained according to the process described in Example 27.

| Elemental microanalysis: | | | |
|---|---|---|---|
| | C % | H % | N % |
| calculated | 50.83 | 7.11 | 6.59 |
| found | 50.62 | 6.96 | 6.15 |
| Melting point: 213° C. | | | |

EXAMPLE 29

N-(2-Dimethylaminocarbonyloxy-3,4-dimethoxy)benzyl-N'-benzylpiperazine dihydrochloride To a solution of 10 mmol of N-benzyl-N'-(3,4-dimethoxy-2-hydroxy)benzyl-piperazine in 100 ml of anhydrous dichloromethane are added dropwise 11 mmol of a solution of N,N-dimethylcarbamoyl chloride in 10 ml of dichloromethane. After stirring at room temperature for 24 h, the formation of a precipitate is observed. After neutralizing with aqueous sodium carbonate solution, the reaction medium is extracted with dichloromethane and the organic phase is concentrated to dryness under partial vacuum, and the residue is chromatographed on a column of silica (eluent: 95/5 dichloromethane/methanol). The fractions retained are combined and then concentrated under partial vacuum and give the expected product.

| Elemental microanalysis: | | | |
|---|---|---|---|
| | C % | H % | N % |
| calculated | 58.36 | 7.25 | 8.17 |
| found | 58.59 | 6.98 | 8.26 |
| Melting point: 229° C. | | | |

EXAMPLE 30

N-(2-Dimethylaminocarbonyloxy-3,4-dimethoxy)benzyl-N'-ethylpiperazine dihydrochloride The expected product is obtained according to the process described in Example 29.

| Elemental microanalysis: | | | |
|---|---|---|---|
| | C % | H % | N % |
| calculated | 53.10 | 7.80 | 9.29 |
| found | 53.25 | 7.52 | 9.66 |
| Melting point: 190° C. | | | |

The following examples were prepared according to the process of Example 1, starting with the corresponding starting materials.

EXAMPLE 31

N-(3,4-Dimethoxy-2-E-phenylcyclopropylcarbonyloxy)benzyl-N'-formylpiperazine hydrochloride

EXAMPLE 32

N-(3,4-Dimethoxy-2-benzoyloxy)benzyl-N'-formylpiperazine hydrochloride

EXAMPLE 33

N-(3,4-Dimethoxy-2-E-(S,S)-phenylcyclopropylcarbonyloxy)benzyl-N'-formylpiperazine hydrochloride

EXAMPLE 34

N-(3,4-Dimethoxy-2-E-(R,R)-phenylcyclopropylcarbonyloxy)benzyl-N'-formylpiperazine hydrochloride

EXAMPLE 35

N-(3,4-Dimethoxy-2-E-phenylcyclopropylcarbonyloxy)benzyl-N'-cyclohexylpiperazine dihydrochloride

EXAMPLE 36

N-(3,4-Dimethoxy-2-benzoyloxy)benzyl-N'-cyclohexylpiperazine dihydrochloride

EXAMPLE 37

N-(3,4-Dimethoxy-2-E-(S,S)-phenylcyclopropylcarbonyloxy)benzyl-N'-cyclohexylpiperazine dihydrochloride

EXAMPLE 38

N-(3,4-Dimethoxy-2-E-(R,R)-phenylcyclopropylcarbonyloxy)benzyl-N'-cyclohexylpiperazine dihydrochloride

EXAMPLE 39

N-(3,4-Dimethoxy-2-E-phenylcyclopropylcarbonyloxy)benzyl-N'-phenylpiperazine dihydrochloride

EXAMPLE 40

N-(3,4-Dimethoxy-2-benzoyloxy)benzyl-N'-phenylpiperazine dihydrochloride

EXAMPLE 41

N-(3,4-Dimethoxy-2-E-(S,S)-phenylcyclopropylcarbonyloxy)benzyl-N'-phenylpiperazine dihydrochloride

EXAMPLE 42

N-(3,4-Dimethoxy-2-E-(R,R)-phenylcyclopropylcarbonyloxy)benzyl-N'-phenylpiperazine dihydrochloride

EXAMPLE 43

N-(3,4-Dimethoxy-2-E-phenylcyclopropylcarbonyloxy)benzyl-N'-2-pyridinylpiperazine trihydrochloride

EXAMPLE 44

N-(3,4-Dimethoxy-2-benzoyloxy)benzyl-N'-2-pyridinylpiperazine trihydrochloride

EXAMPLE 45

N-(3,4-Dimethoxy-2-E-(S,S)-phenylcyclopropylcarbonyloxy)benzyl-N'-2-pyridinylpiperazine trihydrochloride

EXAMPLE 46

N-(3,4-Dimethoxy-2-E-(R,R)-phenylcyclopropylcarbonyloxy)benzyl-N'-2-pyridinylpiperazine trihydrochloride

EXAMPLE 47

N-(3,4-Dimethoxy-2-E-phenylcyclopropylcarbonyloxy)benzyl-N'-methylpiperazine dihydrochloride

EXAMPLE 48

N-(3,4-Dimethoxy-2-benzoyloxy)benzyl-N'-methylpiperazine dihydrochloride

EXAMPLE 49

N-(3,4-Dimethoxy-2-E-(S,S)-phenylcyclopropylcarbonyloxy)benzyl-N'-methylpiperazine dihydrochloride

EXAMPLE 50

N-(3,4-Dimethoxy-2-E-(R,R)-phenylcyclopropylcarbonyloxy)benzyl-N'-methylpiperazine dihydrochloride

EXAMPLE 51

N-(3,4-Dimethoxy-2-E-phenylcyclopropylcarbonyloxy)benzyl-N'-4,4'-difluorobenzhydrylpiperazine dihydrochloride

EXAMPLE 52

N-(3,4-Dimethoxy-2-benzoyloxy)benzyl-N'-4,4'-difluorobenzhydryl-piperazine dihydrochloride

EXAMPLE 53

N-(3,4-Dimethoxy-2-E-(S,S)-phenylcyclopropylcarbonyloxy)benzyl-N'-4,4'-difluorobenzhydrylpiperazine dihydrochloride

EXAMPLE 54

N-(3,4-Dimethoxy-2-E-(R,R)-phenylcyclopropylcarbonyloxy)benzyl-N'-4,4'-difluorobenzhydrylpiperazine dihydrochloride

EXAMPLE 55

N-(3,4-Dimethoxy-2-E-phenylcyclopropylcarbonyloxy)benzyl-N'-benzhydrylpiperazine dihydrochloride

EXAMPLE 56

N-(3,4-Dimethoxy-2-benzoyloxy)benzyl-N'-benzhydrylpiperazine dihydrochloride

EXAMPLE 57

N-(3,4-Dimethoxy-2-E-(S,S)-phenylcyclopropylcarbonyloxy)benzyl-N'-benzhydrylpiperazine dihydrochloride

EXAMPLE 58

N-(3,4-Dimethoxy-2-E-(R,R)-phenylcyclopropylcarbonyloxy)benzyl-N'-benzhydrylpiperazine dihydrochloride

EXAMPLE 59

N-(3,4-Dimethoxy-2-E-phenylcyclopropylcarbonyloxy)benzyl-N'-[2-(N-pyrolidinyl)ethyl]piperazine trihydrochloride

EXAMPLE 60

N-(3,4-Dimethoxy-2-benzoyloxy)benzyl-N'-[2-(N-pyrolidinyl)ethyl]-piperazine trihydrochloride

EXAMPLE 61

N-(3,4-Dimethoxy-2-E-(S,S)-phenylcyclopropylcarbonyloxy)benzyl-N'-[2-(N-pyrolidinyl)ethyl]piperazine trihydrochloride

EXAMPLE 62

N-(3,4-Dimethoxy-2-E-(R,R)-phenylcyclopropylcarbonyloxy)benzyl-N'-[2-(N-pyrolidinyl)ethyl]piperazine trihydrochloride

EXAMPLE 63

N-(3,4-Dimethoxy-2-E-phenylcyclopropylcarbonyloxy)benzyl-N'-(4-fluorobenzyl)piperazine dihydrochloride

EXAMPLE 64

N-(3,4-Dimethoxy-2-benzoyloxy)benzyl-N'-(4-fluorobenzyl)piperazine dihydrochloride

EXAMPLE 65

N-(3,4-Dimethoxy-2-E-(S,S)-phenylcyclopropylcarbonyloxy)benzyl-N'-(4-fluorobenzyl)piperazine dihydrochloride

EXAMPLE 66

N-(3,4-Dimethoxy-2-E-(R,R)-phenylcyclopropylcarbonyloxy)benzyl-N'-(4-fluorobenzyl)piperazine dihydrochloride

EXAMPLE 67

N-(3,4-Dimethoxy-2-E-phenylcyclopropylcarbonyloxy)benzyl-N'-isopropylpiperazine dihydrochloride

EXAMPLE 68

N-(3,4-Dimethoxy-2-benzoyloxy)benzyl-N'-isopropylpiperazine dihydrochloride

EXAMPLE 69

N-(3,4-Dimethoxy-2-E-(S,S)-phenylcyclopropylcarbonyloxy)benzyl-N'-isopropylpiperazine dihydrochloride

EXAMPLE 70

N-(3,4-Dimethoxy-2-E-(R,R)-phenylcyclopropylcarbonyloxy)benzyl-N'-isopropylpiperazine dihydrochloride

EXAMPLE 71

N-(3,4-Dimethoxy-2-E-phenylcyclopropylcarbonyloxy)benzyl-N'-propylpiperazine dihydrochloride

EXAMPLE 72

N-(3,4-Dimethoxy-2-benzoyloxy)benzyl-N'-propylpiperazine dihydrochloride

EXAMPLE 73

N-(3,4-Dimethoxy-2-E-(S,S)-phenylcyclopropylcarbonyloxy)benzyl-N'-propylpiperazine dihydrochloride

EXAMPLE 74

N-(3,4-Dimethoxy-2-E-(R,R)-phenylcyclopropylcarbonyloxy)beizzyl-N'-propylpiperazine dihydrochloride

EXAMPLE 75

N-(3,4-Dimethoxy-2-E-phenylcyclopropylcarbonyloxy)benzyl-N'-heptyl-piperazine dihydrochloride

EXAMPLE 76

N-(3,4-Dimethoxy-2-benzoyloxy)benzyl-N'-heptylpiperazine dihydrochloride

EXAMPLE 77

N-(3,4-Dimethoxy-2-E-(S,S)-phenylcyclopropylcarbonyloxy)benzyl-N'-heptylpiperazine dihydrochloride

EXAMPLE 78

N-(3,4-Dimethoxy-2-E-(R,R)-phenylcyclopropylcarbonyloxy)benzyl-N'-heptylpiperazine dihydrochloride

EXAMPLE 79

N-(3,4-dimethoxy-2-E-phenylcyclopropylcarbonyloxy)benzyl-N'-hexadecylpiperazine dihydrochloride

EXAMPLE 80

N-(3,4-Dimethoxy-2-benzoyloxy)benzyl-N'-hexadecylpiperazine dihydrochloride

EXAMPLE 81

N-(3,4-Dimethoxy-2-E-(S,S)-phenylcyclopropylcarbonyloxy)benzyl-N'-hexadecylpiperazine dihydrochloride

EXAMPLE 82

N-(3,4-Dimethoxy-2-E-(R,R)-phenylcyclopropylcarbonyloxy)benzyl-N'-hexadecylpiperazine dihydrochloride

EXAMPLE 83

N-(3,4-dimethoxy-2-E-phenylcyclopropylcarbonyloxy)benzyl-N'-octadecylpiperazine dihydrochloride

EXAMPLE 84

N-(3,4-Dimethoxy-2-benzoyloxy)benzyl-N'-octadecylpiperazine dihydrochloride

EXAMPLE 85

N-(3,4-Dimethoxy-2-E-(S,S)-phenylcyclopropylcarbonyloxy)benzyl-N'-octadecylpiperazine dihydrochloride

EXAMPLE 86

N-(3,4-Dimethoxy-2-E-(R,R)-phenylcyclopropylcarbonyloxy)benzyl-N'-octadecylpiperazine dihydrochloride

EXAMPLE 87

N-(3,4-Dimethoxy-2-E-phenylcyclopropylcarbonyloxy)benzyl-N'-(3-chloropropyl)piperazine dihydrochloride

EXAMPLE 88

N-(3,4-Dimethoxy-2-benzoyloxy)benzyl-N'-(3-chloropropyl)piperazine dihydrochloride

EXAMPLE 89

N-(3,4-Dimethoxy-2-E-(S,S)-phenylcyclopropylcarbonyloxy)benzyl-N'-(3-chloropropyl)piperazine dihydrochloride

EXAMPLE 90

N-(3,4-Dimethoxy-2-E-(R,R)-phenylcyclopropylcarbonyloxy)benzyl-N'-(3-chloropropyl)piperazine dihydrochloride

EXAMPLE 91

N-(2-Acetoxy-3,4-dimethoxy)benzyl-N'-[3-methyl-12-(4-methylphenyl)]-dodecylpiperazine dihydrochloride

EXAMPLE 92

N-(2-Isobutyryloxy-3,4-dimethoxy)benzyl-N'-benzylpiperazine

Melting point: oil

EXAMPLE 93

N-(2-Isobutyryloxy-3,4-dimethoxy)benzyl-N'-formylpiperazine

Melting point: oil

EXAMPLE 94

N-(3,4-Dimethoxy-2-(nicotinoyloxy)benzyl-N'-tritylpiperazine

EXAMPLE 95

N-(2-Isobutyryloxy-3,4-dimethoxy)benzyl-piperazine

The expected compound is obtained by debenzylation of the compound of Example 92, in dimethyl-formamide under hydrogen pressure in the presence of the catalyst 5% Pd/C.

Melting point: oil

The compounds of Examples 96 to 99 were obtained according to the process described in Example 95 and converted into corresponding salts in hydrochloric medium.

EXAMPLE 96

N-(2-tert-Butylcarbonyloxy-3,4-dimethoxy)benzylpiperazine dihydrochloride

Melting point: 230° C.

EXAMPLE 97

N-(3,4-Dimethoxy-2-E-phenylcyclopropylcarbonyloxy)benzyl-piperazine dihydrochloride

EXAMPLE 98

N-(2-Benzoyloxy-3,4-dimethoxy)benzylpiperazine dihydrochloride

EXAMPLE 99

N-(3,4-Dimethoxy-3-nicotinoyloxy)benzylpiperazine trihydrochloride

EXAMPLE 100

N-(3,4-Dimethoxy-2-thioacetoxy)benzyl-N'-ethylpiperazine dihydrochloride

To a solution of 10 mmol of N-(2-acetoxy-3,4-dimethoxy)benzyl-N'-ethylpiperazine described in Example 5 in 50 ml of xylene, under an inert atmosphere, are added, with stirring, 12 mmol of Lawesson's reagent. The reaction medium is maintained at 130° C. for 18 hours. After cooling and evaporation of the solvent, the residue is chromatographed on silica gel with petroleum ether and then with dichioromethane and gives the expected product.

EXAMPLE 101

N-(3,4-Dimethoxy-2-thioacetoxy)benzyl-N'-bennzylpiperazine dihydrochloride

The expected product is obtained according to the process described in Example 31.

PHARMACOLOGICAL STUDY OF THE DERIVATIVES OF THE INVENTION

The compounds of the invention were studied in comparison with trimetazidine (2,3,4-trimethoxybenzylpiperazine).

EXAMPLE 102

Study of the compounds of the invention on the contractile function of the myocardium and on the myocytic energetic metabolic response in the course of an ischemia-reinfusion sequence (isolated rat heart).

The antiischemic effects of trimetazidine are accompanied, during a test carried out on an isolated rat heart, by a reduction in the ischemic acidosis and protection of the ATP-producing mechanisms (Lavanchy et al., *Advances in Studies on Heart Metabolism*, pp. 257–262, 1987). This study was carried out by means of the use of $^{31}$P NMR spectroscopy, this technique allowing the monitoring, on an isolated and infused heart, of the variation in the contents of phosphorylated compounds (ATP, phosphocreatine, inorganic phosphate) and in the intracellular pH. It allows continuous investigation of a number of variables linked with the energetic state of the myocardium and allows a comparative evaluation of the antiischemic properties of several products.

Methods

The isolated rat heart is infused aortically at a constant pressure (100 cm of water) for 30 min. and is then subjected to a partial global ischemia (coronary output reduced to 1.3% of the initial output) for 24 min., and, lastly, the heart is reinfused at constant pressure for 30 min.

Throughout the experiment, NMR spectra corresponding to 3-minute-long acquisitions are recorded. After statistical exploitation, they serve to determine the intracardial concentration of ATP, of phosphocreatine (PC) and of inorganic phosphate (Pi), as well as to evaluate the intracellular pH. From these data, the kinetic changes in these variables during the ischemia and during the reinfusion can be determined.

Experimental procedure

This procedure is intended to assess the effect of the presence of the product before and during the ischemia. To this end, the product is administered in the infusion medium after normoxic infusion for 20 min; it remains present in the infusion solution throughout the remainder of the experiment. A concentration of $5\times10^{-6}$M was chosen for this comparative study.

1st experimental series

This is intended to evaluate the effects of the products on the heart function. The heart is infused under the conditions defined above, and a catheter connected to a pressure sensor is introduced into the left ventrical (via the atrium) in order to monitor the pressure changes developed by the LV. The heart rate and the heart output are also monitored.

2nd experimental series

This is carried out in a superconducting magnet of 5.9 T in order to record the $^{31}$P NMR spectra. This series of experiments is intended to evaluate the impact of the product on the energetic equilibrium of the myocardium both in normoxia, in ischemia and in reinfusion.

Results

The results obtained in this study show that the cytoprotective effect of trimetazidine during an ischemia-reinfusion sequence of the myocardium is found to be greatly increased with the compounds of the invention and more particularly with the compound of Example 1, which even exerts a statistically significant effect on the intracellular ATP content. The effect of the compound of Example 1 is also particularly pronounced on the intracellular acidosis induced by the ischemia: the intracellular pH falls from pH 7.2 to pH 6.0 at the end of the ischemia in the control groups, it is maintained at pH 6.35 in the group treated with trimetazidine and at pH 6.5 in the group treated with the compound of Example 1, which, in physiopathological terms, is a considerable difference.

EXAMPLE 103

Activity on mitochondrial energy production during an experimental calcium overload The mitochondrian plays an essential part in cellular energy production in the form of ATP. The situation of cellular hypoxia following an ischemia leads to an intracellular calcium overload (Marban et al., 80, 17–22, 1989) and in particular a mitochondrial calcium overload, which is associated with the fall in the synthesis of ATP: it has been demonstrated that the exaggerated storage of calcium by the mitochondrian lowered ATP synthesis (Tuena de Gomez-Puyou et al., *Biochem. Biophys. Acta,* 532, 396–405, 1980) and that this calcium excess was the cause of the cell disorders characteristic of ischemic pathologies (Cheung et al., *New Engl. J. Med.,* 314, 1670–1676, 1986).

This lowering in mitochondrial ATP synthesis can be created experimentally on isolated mitochondria placed in a medium containing cyclosporin A. The latter blocks the extrusion of mitochondrial $Ca^{2+}$ causing the accumulation of $Ca^{2+}$ ions in the mitochondrian and a decrease in ATP-producing oxidative phosphorylation (Crompton et al., 1988; Broekemeier et al., *Biochem. J.,* 255, 357–360, 1989).

Equipment and method

The procedure followed is the one described by Salducci et al. (*J. Pharmacol. Exp. Ther.,* 277, 417–422, 1996). Briefly, the mitochondria are extracted from rat livers. Mitochondrial respiration (1.5 mg of proteins placed in a reaction chamber) is brought about by the addition of sodium succinate, which is used as substrate (at $6\times10^{-4}$M) and oxidative phosphorylation is triggered by the addition of ADP to the survival medium up to a final concentration of $1\times10^{-5}$M.

By recording the rates of oxygen consumption (in nmol/min./mg of mitochondrial protein) it is possible to calculate the characteristic parameters of the mitochondrial energy synthesis in the form of ATP.

Results

The results obtained in this study show that the compounds of the invention significantly restore mitochondrial ATP synthesis. The compounds of the invention allow a restoration of between 80 and 100%. At a concentration of $1\times10^{-6}$M, 100% restoration was observed with the compound of Example 1, whereas this restoration is only 47% with trimetazidine.

EXAMPLE 104

Study of the ability of chemical substances to cross the blood/brain barrier

Description of the blood/brain barrier model

In order to study the functions of cerebral capillaries "in vitro", we developed a coculture model which allows the "in vivo" situation to be recreated. The endothelial cells of capillaries and astrocytes are cultured on either side of a filter.

The endothelial cells are cultured in the upper compartment on the filter and the astrocytes in the lower compartment on the bottom of the Petri dish.

Under these conditions, the cells retain all the markers of endothelial cells (presence of factor VIII, non-thrombogenic surface, production of prostacycline, presence of conversion enzyme) and of the blood-brain barrier (presence of tight junctions, rarity of pinocytosis vesicles, presence of monoamine oxydase and γ-glutamyl transpeptidase (Dehouck et al., *J. of Controlled Release.,* 21, 81–92, 1992). Method (Dehouck et al., *J. of Controlled Release,* 21, 81–92, 1992). On the day of the experiment, a solution of Ringer-HEPES (150 mM NaCl; 5.2 mM KCl; 2.2 mM $CaCl_2$; 0.2 mM $MgCl_2 \cdot 6H_2O$; 6 mM $NaHCO_3$; 5 mM HEPES; 2.8 mM glucose) is placed in the lower compartment of a 6-well dish (3 ml per well). A filter of covered with a monolayer of endothelial cells is transferred into the first well of the 6-well dish. 2 ml of the Ringer-HEPES solution containing the test compound are placed in the upper compartment of the filter. The filters are transferred into another well of the 6-well dish 10, 20, 30, 60, 90 and 120 minutes after addition of the compound, in order to reduce to a minimum the possible passage of the compound from the lower compartment to the upper compartment. The experiments are performed in triplicate with filters covered with a monolayer of endothelial cells from cerebral capillaries or of collagen alone as control. They are agitated at 37° C. throughout the experiment.

Analysis of the results

Determination of the coefficient of permeability

In order to determine the coefficients of permeability of the compounds, the clearance of each substance is determined according to the formula:

$$\text{clearance } (\mu l) = Cl\,(\mu l) = \frac{X}{Cd}$$

where X is the amount of substance in the lower compartment, where Cd is the concentration of substance in the upper compartment.

The clearance increases linearly with time for 60 minutes. In the graph clearance=f(t), measurement of the slope gives the value "PSt" where PS=permeability×surface area of the monolayer (in $\mu l$/min) for the filters covered with cerebral capillary endothelial cells. "PSf" is calculated in the same way for the control filters. The permeability for the monolayer of endothelial cells alone (PSe) is given by:

$$\frac{1}{PSe} = \frac{1}{PSt} - \frac{1}{PSf}$$

The coefficient of endothelial permeability "Pe" is calculated by dividing "PSe" by the surface area of the monolayer of endothelial cells. "Pe" is expressed in "cm/min".

Conclusion

Trimetazidine is characterized by an extremely low coefficient of permeability of the blood/brain barrier (0.42), indicating that the compound penetrates poorly into the brain and that it cannot be envisaged for use in the treatment of cerebral pathologies.

As regards the compounds of the invention, they have a markedly higher coefficient of permeability of the blood-brain barrier.

In contrast, the compounds of Examples 1, 2, 17 and 19 in particular, which have a coefficient of permeability of the blood/brain barrier of greater than 1, penetrate the brain very easily, in a manner exactly proportional to their concentration in the circulatory stream.

EXAMPLE 105

Pharmaceutical composition

Preparation formula for 1000 tablets containing a 10 mg dose

Compound of Example 1 10 g
Hydroxypropylcellulose 2 g
Wheat starch 10 g
Lactose 100 g
Magnesium stearate 3 g
Talc 3 g

We claim:

1. A compound selected from those of formula (I)

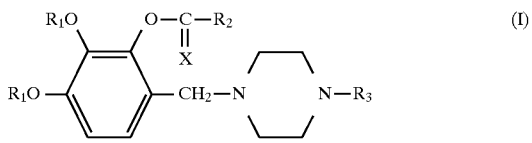

in which:
R$_1$ represents linear or branched (C$_1$–C$_6$)alkyl,
x represents oxygen or sulfur,
R$_2$ represents linear or branched (C$_1$–C8)alkyl (optionally substituted with carboxyl or linear or branched (C$_1$–C$_6$) alkoxycarbonyl), linear or branched (C$_1$–C$_6$)alkoxy, a phenyl (optionally substituted with one or more halogen or linear or branched (C$_1$–C$_6$)alkyl, linear or branched (C$_1$–C$_6$)alkoxy, hydroxyl or trihalomethyl), (C$_3$–C$_7$)cycloalkyl (optionally substituted with one or more phenyl which are themselves optionally substituted with one or more halogen or linear or branched (C$_1$–C$_6$)alkyl, linear or branched (C$_1$–C$_6$)alkoxy, hydroxyl or trihalomethyl), 4-(2,3-dithiacyclopent1-yl) butyl, pyridyl, amino (optionally substituted with one or two linear or branched (C$_1$–C$_6$)alkyl), or any one of the following groups:

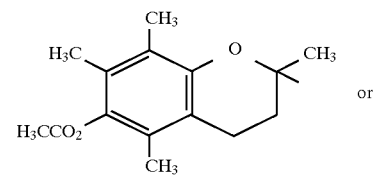

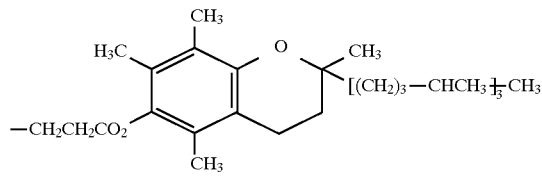

wherein
R$_3$ represents hydrogen, (C$_3$–C$_7$)cycloalkyl, formyl, phenyl (optionally substituted with one or more halogen or linear or branched (C$_1$–C$_6$)alkyl, linear or branched (C$_1$–C$_6$)alkoxy, hydroxyl or trihalomethyl), pyridyl, or linear or branched (C$_1$–C$_{20}$)alkyl optionally substituted with one or more, identical or different, halogen or groups selected from the following:
phenyl optionally substituted with one or more halogen or linear or branched (C$_1$–C$_6$)alkyl, linear or branched (C$_1$–C$_6$)alkoxy, hydroxyl or trihalomethyl, (C$_3$–C$_7$)cycloalkyl (optionally substituted with one or more phenyl which are themselves optionally substituted with one or more halogen or linear or branched (C$_1$–C$_6$)alkyl, linear or branched (C$_1$–C$_6$) alkoxy, hydroxyl or trihalomethyl),
linear or branched (C$_1$–C$_6$)alkoxy,
hydroxyl or
pyrrolidinyl,
the optical isomers thereof and the addition salts thereof with a pharmaceutically-acceptable acid or base.

2. A compound of claim 1, wherein X represents oxygen.
3. A compound of claim 1, wherein X represents sulfur.
4. A compound of claim 1, wherein R$_1$ represents methyl.
5. A compound of claim 1, wherein R$_2$ represents (C$_3$–C$_7$) cycloalkyl optionally substituted with phenyl which is itself optionally substituted as indicated in claim 1.

6. A compound of claim 4, wherein $R_2$ represents phenylcyclopropyl.

7. A compound of claim 1, wherein $R_3$ represents alkyl optionally substituted as indicated in claim 1.

8. A compound of claim 1, which is N-(3,4-dimethoxy-2-E-phenylcyclopropylcarbonyloxy)benzyl-N'-ethylpiperazine, the optical isomers thereof and the addition salts thereof with a pharmaceutically-acceptable acid.

9. A method for treating a living body afflicted with a condition selected from chronic or cellular ischemia comprising the step of administering to the living body an amount of a compound of claim 1 which is effective for alleviation of said condition.

10. A pharmaceutical composition useful in treating chronic or cellular ischemia comprising as active principle an effective amount of a compound as claimed in claim 1, together with one or more pharmaceutically-acceptable excipients or vehicles.

* * * * *

UNITED STATES PATENT AND TRADEMARK OFFICE
CERTIFICATE OF CORRECTION

PATENT NO. : 5,849,745           Page 1 of 2
DATED      : Dec. 15, 1998
INVENTOR(S): M. Wierzbicki, M.-F. Boussard,
             S. Labidalle, D. Guyot, Y. Rolland,
             J. P. Tillement, B. Testa, A. Creyat It is certified that error appears in the above-indentified patent and that said Letters Patent is hereby corrected as shown below:

Column 8, line 23(approx.): "4-dinethoxy}" should read
    -- 4-dimethoxy} --.

Column 8, line 40: "dinethoxy}" should read
    -- dimethoxy} --.

Column 11, line 27(approx.): "N-(2-Ethoxyearbonyloxy" should read -- N-(2-Ethoxycarbonyloxy --.

Column 16, line 22: At the end of the line,
    "beizzyl-N'-" should read -- benzyl-N'- --.

Column 18. line 50: "dichioromethane" should read
    -- dichloromethane --.

Column 20, line 66: "A filter of covered" should read
    -- A filter covered --.

Column 21, line 60: "Example 110 g" should read
    -- Example 1  10 g --.

UNITED STATES PATENT AND TRADEMARK OFFICE
CERTIFICATE OF CORRECTION

PATENT NO. : 5,849,745
DATED : Dec. 15, 1998
INVENTOR(S) : M. Wierzbicki, M.-F. Boussard, S. Labidalle, D. Guyot, Y. Rolland, J. P. Tillement, B. Testa, A. Crevat It is certified that error appears in the above-indentified patent and that said Letters Patent is hereby corrected as shown below:

Column 21, line 67: "We claim:" should be at the top of Column 22.

Signed and Sealed this

Eleventh Day of May, 1999

Attest:

Q. TODD DICKINSON

*Attesting Officer*          *Acting Commissioner of Patents and Trademarks*